United States Patent [19]

Jakobson et al.

[11] Patent Number: 5,510,542
[45] Date of Patent: Apr. 23, 1996

[54] PROCESS AND APPARATUS FOR PRODUCING DIGLYCERIN

[75] Inventors: Gerald Jakobson; Werner Siemanowski, both of Rheinberg, Germany

[73] Assignee: Solvay Fluor und Derivate GmbH, Hanover, Germany

[21] Appl. No.: 387,949

[22] Filed: Feb. 24, 1995

[30] Foreign Application Priority Data

Aug. 25, 1992 [DE] Germany ............ 42 28 147.4

[51] Int. Cl.$^6$ ............ C07C 41/02; C07C 43/10; B01J 14/00
[52] U.S. Cl. ............ 568/680; 422/193
[58] Field of Search ............ 568/680; 422/193

[56] References Cited

U.S. PATENT DOCUMENTS

| | | | |
|---|---|---|---|
| 2,520,670 | 8/1950 | Wittcoff et al. | 568/680 |
| 3,548,010 | 12/1970 | Yoshino et al. | 568/680 |
| 4,243,636 | 1/1981 | Shiraki et al. | 422/193 |
| 4,952,375 | 8/1990 | Zardi | 422/193 |
| 4,960,953 | 10/1990 | Jakobson et al. | |
| 4,973,763 | 11/1990 | Jakobson et al. | 568/680 |
| 4,992,594 | 2/1991 | Jakobson et al. | 568/680 |
| 5,041,688 | 8/1991 | Jakobson et al. | |
| 5,154,255 | 9/1992 | Shimada et al. | 422/193 |
| 5,243,086 | 9/1993 | Jakobson et al. | 568/680 |
| 5,349,094 | 9/1994 | Harris et al. | 568/680 |

FOREIGN PATENT DOCUMENTS

| | | |
|---|---|---|
| 333984 | 9/1989 | European Pat. Off. |
| 374699 | 6/1990 | European Pat. Off. |
| 1132490 | 3/1957 | France |

*Primary Examiner*—Joseph E. Evans
*Attorney, Agent, or Firm*—Evenson, McKeown, Edwards & Lenahan

[57] ABSTRACT

A process for producing diglycerin having a low content of cyclic components by reacting glycerin with epichlorohydrin by a continuous process in which the epichlorohydrin required for the reaction is introduced into at least one flow reactor at several separate spots or reaction zones mutually separated in space in the direction of flow; the reacted reaction mixture is substantially freed of excess glycerin in at least one evaporator; the remaining chlorohydrin/ether mixture is hydrolyzed in at least one first step with a 5 to 40 mole % excess alkali carbonate solution, calculated with respect to organically bound chlorine in the chlorohydrin ether, at a pH of 6.5 to 9.5, and hydrolysis is at least substantially completed in a second step with an alkali hydroxide at a pH above 10; the resulting hydrolyzed crude product solution is adjusted to a pH of 5.5 to 8 with a mineral acid, preferably hydrochloric acid; and the resulting solution is condensed, precipitating salts are removed, and the diglycerin solution containing less than 8% by weight residual inorganic salts is freed of cyclic diglycerin and residual glycerin in a flash evaporator. Apparatus for carrying out the foregoing method is also disclosed.

24 Claims, 1 Drawing Sheet

PROCESS AND APPARATUS FOR PRODUCING DIGLYCERIN

This application is a 371 of PCT/EP93/02261 filed Aug. 23, 1993.

The present invention relates to a process for the production of diglycerin, which is low in cyclic constituents, by reacting glycerin with epichlorhydrin at temperatures of 20° to 120° C., preferably 50° to 100° C., in the presence of an acid catalyst and at a molar ratio of glycerin to epichlorhydrin of 20:1 to 1:1, preferably 12:1 to 5:1, in which case subsequently the excess glycerin is removed from the resulting reaction mixture, and the remaining chlorhydrin ether mixture or reaction mixture is reacted at a temperature of 60° to 120° C., preferably 80° to 110° C., (corresponding to the content of organically bound chlorine in the reaction mixture) with an alkaline reacting medium, preferably an alkaline reacting aqueous solution.

Diglycerin (bis-(2,3-dihydroxypropyl)ether) is a polyol which is versatile in its use as a moisturizer and viscosity enhancing agent in cosmetic products and as a starting product for various derivatives, primarily surface-active compounds. In the known processes for the production of diglycerin, a mixture of diglycerin and higher polyglycerins is obtained as the reaction product, the product mixture also having a more or less high proportion of glycerin and cyclic polyglycerins. However, for the above-mentioned applications of diglycerin, it is necessary that the proportion of diglycerin in the polyglycerin mixture be as high as possible and the contents of glycerin and cyclic constituients be very low.

From European Patent Document EP-A 0 374 699, a process already is known for producing polyglycerins which have a proportion of more than 50% by weight diglycerin and are low in cyclic constituents. The production takes place by the reaction of glycerin with epichlorhydrin at temperatures of from 20° to 140° C., preferably 60° to 100° C., in the presence of an acid catalyst and at a molar ratio of glycerin to epichlorhydrin of from 10:1 to 1:1, preferably 6:1 to 1.4:1, in which case subsequently the resulting reaction mixture, which optionally is freed of excess glycerin, is reacted at a temperature of from 50° to 120° C., preferably 60° to 95° C., corresponding to the content of organically bound chlorine, with an alkaline reacting medium, preferably an alkaline reacting aqueous solution. Subsequently, a further working up or purification of the resulting reaction mixture takes place, in which case, after the addition of water, the glycerin—polyglycerin mixture is deionized by means of one or more ion exchangers; is dehydrated by distillation; and is finally separated by fractional distillation into glycerin, diglycerin and higher polyglycerins.

It was an object of the present invention to modify the known process such that, when the reaction is carried out continuously, a further increase is achieved of the diglyglycerin content in the polyglycerin mixture so that a product is obtained which preferably has a proportion of more than 80% by weight of diglycerin and is low in cyclic constituents. Furthermore, the increase of the diglycerin content should be realized in an economical process which, at the same time, permits a simplified working up of the reaction mixture and an advantageous reduction of undesired constituents so that the quality of the reaction product likewise can be improved.

In accordance with the invention, it has been found that this object is achieved by means of a process in which the production of diglycerin, which is low in cyclic constituents, takes place by the reaction of glycerin with epichlorhydrin at temperatures of 20° to 120° C., preferably 50° to 100° C., in the presence of an acid catalyst and at a molar ratio of glycerin to epichlorhydrin of 20:1 to 1:1, preferably 12:1 to 5:1, in which case, in a continuous implementation of the reaction, the epichlorhydrin required for the reaction is introduced into at least one flow reactor at several points or reaction zones which are spatially separate from one another in the flow direction. The reacted reaction mixture thereafter is largely freed of or separated from excess glycerin in at least one evaporating device, and the remaining chlorhydrin ether mixture is hydrolyzed at a temperature of 60° to 120° C., preferably 80° to 110° C., in a first stage with an aqueous alkali carbonate solution at an excess of 5 to 40 molar %, preferably 15 to 25 molar %, calculated with respect to the organically bound chlorine of the chlorhydrin ether, and in a pH-range of 6.5 to 9.5, preferably 7 to 8.5, and in a second stage, the hydrolysis is carried out to completion by means of alkali hydroxide, preferably an aqueous alkali hydroxide solution, at a pH-value of above 10. After the completion or substantial completion of the hydrolysis, the crude product solution is adjusted by addition of a mineral acid, preferably hydrochloric acid, to a pH-value of 5.5 to 8, preferably 6 to 7, and the resulting solution is evaporated, whereby the precipitating salts are separated, and subsequently the diglycerin solution which contains an under 8% by weight residual content of inorganic salts is freed from cyclic diglycerin and the residual proportions of glycerin by distillation in at least one flash evaporator.

The process according to the invention makes it possible to continuously carry out the reaction of epichlorhydrin with glycerin and to produce a diglycerin which is not only low in cyclic constituents but which, even as a crude product before the final distillative treatment, has a very low content of glycerin, whereby the proportion of open-chained diglycerin in the raw product already amounts to over 80% by weight.

The advantageous improvement with respect to the yield of diglycerin is achieved particularly as the result of two measures according to the invention: firstly, the epichlorhydrin required for the reaction is introduced into at least one flow reactor at several points or reaction zones which are spatially separated from one another in the flow direction so that the epichlorhydrin stream is divided into several partial streams, whereby, corresponding to the number of introduced partial streams, a plurality of reaction zones or reaction centers are formed in the flow reactor at which the reaction of glycerin and epichlorhydrin to diglycerin as the main product of the synthesis takes place; and secondly the unreacted glycerin is separated in a distillation device immediately after the reaction mixture emerges from the flow reactor. The substantial removal of the glycerin by means of relatively simple distillative methods is possible only in this stage of the process according to the invention. In addition, in this manner the volume of the stream which is treated in a subsequent hydrolysis by means of alkaline media can be significantly reduced.

According to one advantageous embodiment, the content of excess glycerin used in the reaction mixture is reduced in at least one evaporating device, preferably a continuously operated evaporating device, to below 20% by weight (relative to the reaction mixture), preferably to below 10% by weight, and particularly to below 3% by weight.

Thin-film evaporators and/or flash evaporators, preferably a combination of these two types of evaporators, are particularly suitable for use as the evaporating devices. The glycerin obtained as a head product has a mass content of >98% and may be recycled to the process.

The two-stage hydrolysis according to the invention of the chlorhydrin ether mixture, which follows the above-mentioned process step, enables a complete substitution of each of the organically bound chlorines by respective OH-groups so that the corresponding polyglycerin compounds are obtained.

In the case of the known processes, it was found that complete reaction of the chlorhydrin ethers could not be achieved in a single hydrolysis stage by means of an alkali carbonate solution, so that in this case up to 10% of the chlorhydrin ethers remained in the reaction solution and a diglycerin is obtained which still contains organically bound chlorine. It is not possible to separate the chlorhydrin ether from the glycerin by means of a thin-film or flash evaporator.

In accordance with the invention, the advantageous complete reaction of the organically bound chlorine takes place particularly in the second hydrolysis stage by means of an aftertreatment of the residual chlorhydrin ether with alkali hydroxide at a pH-value of above 10. According to the invention, it has been found in this case that the adjustment of the pH-value >10 is critical for the effectiveness of the second treatment stage.

In order to achieve, following the hydrolysis, a substantial desalination of the product mixture and thus a decrease in the viscosity of the crude product solution after the evaporation, the alkaline crude product solution is adjusted by means of a mineral acid, preferably hydrochloric acid, to a pH-range of 6.5 to 9.5, preferably 7 to 8.5. In this manner, easily filtrable salts are obtained after the evaporation of the solution.

According to a preferred embodiment of the process of the invention, the crude product solution, which has been treated with mineral acid, is concentrated in a flash evaporator and is subsequently freed of precipitated salts by means of filtration or centrifugation.

The resulting crude diglycerin solution is desalted by this process step to such an extent that by means of a subsequent, simple distillation in at least one flash evaporator, cyclic diglycerin and residual proportions of glycerin can be removed and finally diglycerin is obtained in high yield and purity.

According to another advantageous embodiment of the process according to the invention, the proportion of diglycerin in the crude product may be increased by introducing the epichlorhydrin in two or more partial streams in at least one flow reactor which is subdivided by constrictions in its cross-section into two or more individual chambers or reaction zones, in which case at least one partial stream is preferably introduced into each individual chamber or reaction zone.

The increase of the diglycerin content in the crude product according to the invention may also be boosted by dividing the total flow of the epichlorhydrin required for the reaction into two partial streams, and introducing a first partial stream into a first flow reactor at several points or reaction zones which are spatially separated from one another in the flow direction, and subsequently continuously transferring the reaction mixture to a second flow reactor where the second partial flow of the epichlorhydrin is fed in in a metered fashion, preferably at several points or reaction zones which are spatially separated from one another in the flow direction.

According to another advantageous embodiment of the process of the invention, the introduction of the epichlorhydrin into the flow reactor takes place in such a way that the ratio of glycerin to epichlorhydrin in the individual reaction zones, preferably in the area and/or in the proximity of the inlet opening or inlet point for the epichlorhydrin, is greater than the preselected overall ratio of glycerin to epichlorhydrin of 20:1 to 1:1, preferably 12:1 to 5:1.

According to an advantageous embodiment, in the first hydrolysis stage of the process according to the invention, a higher than 1.5-molar, preferably a higher than 2-molar, soda solution is utilized in order to already achieve a high rate of conversion of the organically bound chlorine in this first hydrolysis stage.

In the second hydrolysis stage, preferably a soda lye of more than 10% by weight is used, particularly a soda lye of more than 35% by weight.

According to a preferred embodiment of the process of the invention, the residence time of the reaction mixture in the first stage of the hydrolysis is set at a time period of more than 1 hour, preferably at more than 1.5 hours, and the residence time in the second hydrolysis stage is set at more than 0.5 hours, preferably at more than 0.75 hours.

In order to effect complete desalination, the product solution, which has been freed of glycerin and cyclic diglycerin by distillation, can be treated by means of ion exchangers, preferably a combination of several basic cation exchangers and at least one acidic anion exchanger, whereby the diglycerin/polyglycerin solution is first diluted with water.

After the product solution has been passed through the ion exchangers, a water can again be removed by evaporation and subsequently a distillative separation may be carried out into diglycerin and higher polyglycerins.

The invention also relates to an improved apparatus for carrying out the process according to the invention. This apparatus contains or comprises a reactor or reaction vessel, preferably a vertically arranged flow reactor with a cylindrical reactor housing, having at least one inlet for the glycerin and the catalyst at the lower end and having at least one outlet for the reaction mixture at the upper end, having at least one stirring shaft which is coaxially and centrally arranged in the reactor or reaction vessel and on which at least one stirring device is attached, and having a supply conduit for the epichlorhydrin which is arranged parallel to the stirring shaft and opens in several conduit ends or conduit openings at different levels into the reactor space, at least one evaporating device, preferably a thin-film and/or flash evaporator, at least one reaction vessel for carrying out the hydrolysis, at least one reaction vessel for carrying out the subsequent hydrolysis, and at least one additional flash evaporator, whereby the reaction space is subdivided by constrictions in its cross-section into at least two, preferably more than three reaction zones or reaction chambers, the supply conduit for the epichlorhydrin is arranged within the reactor space separated a distance from the outer circumference of the stirring device or devices, and at least one conduit end or conduit opening of the supply conduit for the epichlorhydrin opening into each reaction zone or reaction chamber and at least one stirring device being attached to the stirring shaft in each reaction zone or reaction chamber.

In the following, the apparatus according to the invention and its advantageous embodiments will be described with reference to FIG. 1 of the drawing.

The reactor or reaction vessel 1, which is preferably constructed as a vertically arranged flow reactor or as a reaction column with a cylindrical reactor housing, has on its lower end, preferably in the reactor bottom, an inlet or a supply conduit through which the glycerin reaction educt 9 with the added catalyst is introduced into the reactor; at the upper end of the reactor, preferably above the uppermost or highest cross-sectional constriction, there is an outlet or a discharge line through which the formed reaction mixture 3 is discharged from the reactor. The introduction of the educt stream and/or the discharge of the product stream may be aided by the use of pumps.

Furthermore, a coaxial stirring shaft 2 is arranged centrally in the reactor space which is continuously rotatable and on which at least one stirring device 10 is attached. Such a stirring device may, for example, consist of a disk stirrer. Parallel to the axis of the stirring shaft, the apparatus according to the invention has a tubular conduit 7 through which the epichlorhydrin 6 is conveyed into the reactor space. In accordance with the invention, the supply conduit 7 is arranged inside the reactor space separated a distance from the outer circumference of the stirring device or devices. It opens in several conduit ends or conduit openings 8 at different levels into the reactor space, in which case the latter is subdivided by means of constrictions in its cross-section into at least two, preferably more than three, reaction zones or reaction chambers 4, and at least one conduit end or conduit opening 8 of the supply conduit for the epichlorhydrin and at least one stirring device 10 fastened on the stirring shaft are provided in each reaction zone or reaction chamber.

As a result of the division of the reaction space into several reaction zones, into each of which at least one partial stream of the epichlorhydrin is introduced into the mixture of glycerin and the catalyst through a respective one conduit end or one conduit opening of the supply conduit 7, a number of reaction centers are formed, corresponding to the number of partial streams which are introduced, in which the reaction of glycerin and epichlorhydrin takes place with a surprisingly higher yield of diglycerin than in the case of the known processes.

Although, in accordance with the invention, this higher yield of diglycerin is obtained simply by introducing the epichlorhydrin into the flow reactor at several points which are spatially separated from one another in the flow direction, as a result of the formation of individual reaction zones or reaction chambers, by means of the introduction of constrictions in the cross-section and as a result of the continuous mixing of the reaction mixture in each chamber by means of at least one stirring device, a very favorable ratio of glycerin to epichlorhydrin is produced so that the yield can be further improved as a result of the construction of the flow reactor in accordance with the invention.

This improvement of the yield is also promoted by the fact than, according to a preferred embodiment of the apparatus according to the invention, the constrictions in cross-section are constructed in a particular manner. Accordingly, they are made of intermediate base plates, deflecting plates or separator plates 5 which have a plurality of perforations or through-openings for the reaction mixture. In this way, an unimpaired mixing of the product solutions formed in the individual reaction centers and a free-flowing upward-directed flow of the reaction mixture in the reactor space are assured.

According to another advantageous embodiment of the apparatus according to the invention, the intermediate base plates, the deflecting plates or the separator plates have a circular construction and are arranged horizontally at different levels in the reactor space, whereby the intermediate base plates, deflecting plates or separator plates each have a central opening through which the stirring shaft extends and an opening through which the supply conduit for the epichlorhydrin passes.

The free guidance and the mixing of the product streams and/or of the reaction constituents may be further improved in that an unsealed gap is formed between the reactor wall and the outer margin of the intermediate base plates, deflecting plates or separator plates.

Moreover, it has been found to be advantageous for the intermediate bottom plates, deflecting plates or separator disks to have approximately the same spacing from one another so that reaction zones or reaction chambers of approximately equal size are formed.

According to another preferred embodiment of the apparatus according to the invention, the mixing of the reaction constituents is increased by constructing the conduit ends or conduit openings of the supply conduit for the epichlorhydrin as Venturi nozzles.

A single reactor or a single reaction column may be used in the apparatus according to the invention. However, two or more reactors of the type according to the invention may also be used which are connected in series, whereby the overall epichlorhydrin stream is once again separated into a higher number of partial streams.

Figure 1:
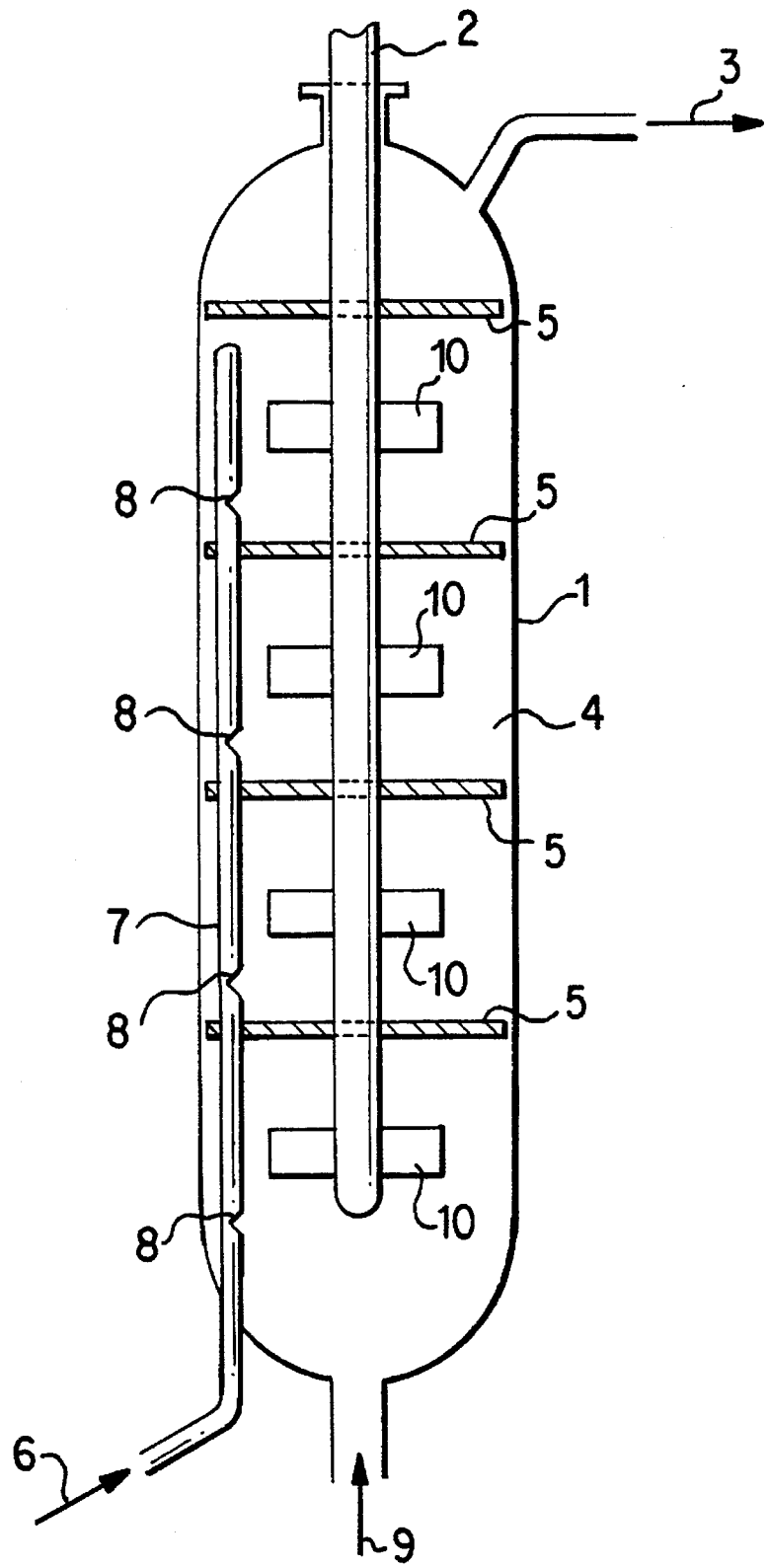
FIG. 1.

Schematic representation of a reaction vessel for explaining the apparatus according to the invention and the process according to the invention; the meaning of reference numbers 1 through 10 is found in the foregoing description.

The following working embodiment has the purpose of explaining the invention without being limited to it.

Working Embodiment

Within one hour 5.526 kg ($\approx$60 mole) of glycerin mixed with a catalytic quantity of sulfuric acid are introduced into a flow reactor (1-liter double-wall reactor made of glass with a stirrer and two conduits which are spatially separated from one another in the flow direction for introducing controlled amounts of the epichlorhydrin), and 0.695 kg ($\approx$7.5 mole) of epichlorhydrin in two partial streams are metered into the flow reactor, while a reaction temperature of from 60° to 70° C. is maintained by cooling via the double wall.

The discharge of the reactor is conveyed to a combination of a thin-film evaporator and flash evaporator and the excess glycerin used is removed from the reaction mixture by distillation (residual content of glycerin in the chlorhydrin ether mixture $\leq$3%). The sump discharge of the evaporator device is conducted to a buffer vessel and subsequently the chlorhydrin ether mixture is converted in portions through a 2-stage hydrolysis, 1st Stage: Addition of 2.5-molar soda solution (20 mole-% excess of sodium carbonate, reaction time approx. 2 hours, reaction temperature approx. 95° C., pH-value 7–8.5)

2nd Stage: Addition of 50% soda lye (approx. 10 to 15%, relative to the quantity of 2.5-molar soda solution used, reaction time approx. 1 hour, pH-value 10.5), to a crude diglycerin/polyglycerin mixture.

The resulting aqueous diglycerin/polyglycerin solution is adjusted to a pH-value of from 6 to 7 with concentrated hydrochloric acid and is subsequently concentrated by evaporation under vacuum, while precipitated portions of salt are separated by filtration.

The product solution, which still contains salts (residual salt content below 8% by weight) is freed of glycerin and cyclic diglycerin by distillation in a thin-film evaporator, and the sump discharge of the evaporator is completely desalted by means of a combination of acidic and basic ion exchangers (after prior addition of water); is then concentrated by evaporation, and is separated by distillation into diglycerin and higher polyglycerins.

A GC-analysis of the desalted and dehydrated crude diglycerin/polyglycerin solution after the two-stage hydrolysis yields in the following composition (numerical values each relate to g/kg):

glycerin 20 cycl. diglycerin 30 diglycerin 830 cycl. triglycerin 20 triglycerin 80 cycl. tetraglycerin 5 tetraglycerin 10 pentaglycerin 5

We claim:

1. A process for continuously producing diglycerin having a low content of cyclic constituents, said process comprising the steps of:

reacting glycerin in at least one continuous flow reactor with epichlorohydrin introduced into said at least one flow reactor at a plurality of spatially separated reaction zones at an overall molar ratio of glycerin to epichlorohydrin of 20:1 to 1:1, a temperature of from 20° to 120° C. and in the presence of an acid catalyst to produce a diglycerin-containing reacted mixture;

subsequently removing excess glycerin from said mixture by evaporation in at least one evaporation device to obtain a chlorohydrin and ether mixture;

hydrolyzing the chlorohydrin and ether mixture in a first hydrolysis stage at a temperature of 60° to 120° C. and a pH of 6.5 to 9.5 with a 5 to 40 mole-% excess of an alkaline reacting alkali carbonate solution calculated with respect to organically bound chlorine in the chlorohydrin and ether mixture, completing hydrolysis of said chlorohydrin and ether mixture in a second hydrolysis stage at a pH of above 10 with alkali hydroxide to obtain a hydrolyzed crude product solution;

adjusting the hydrolyzed crude product solution to a pH of 5.5 to 8 by addition of a mineral acid;

concentrating the resulting solution and separating precipitated salts to obtain a diglycerin solution containing less than 8% by weight of residual inorganic salts; and freeing the diglycerin solution of cyclic diglycerin and any residual glycerin by distillation in at least one flash evaporator.

2. A process according to claim 1, wherein said reacting step is carried out at a molar ratio of glycerin to epichlorohydrin of 12:1 to 5:1 and at a temperature in the range from 50° to 100° C.;

in the first hydrolysis stage the chlorohydrin and ether mixture is treated with a 15 to 25 mole-% excess of an aqueous alkali carbonate solution at a temperature of 80° to 110° C. and at a pH of 7 to 8.5;

in the second hydrolysis stage the alkali hydroxide is an aqueous alkali hydroxide solution; and the hydrolyzed crude product solution is adjusted to a pH of 6 to 7 by adding hydrochloric acid.

3. A process according to claim 1, wherein said at least one flow reactor is divided by means of cross-sectional constrictions into at least two individual reaction zones, and the epichlorohydrin is introduced into said flow reactor in at least two partial streams, at least one of said partial streams being introduced into each individual reaction zone of the reactor.

4. A process according to claim 1, wherein a portion of the epichlorohydrin required for reaction with the glycerine is introduced into a first continuous flow reactor at a plurality of spatially separated points along the flow to form a reaction mixture;

the reaction mixture is continuously transferred from said first continuous flow reactor to a second continuous flow reactor, and the balance of the epichlorohydrin required for reaction with the glycerine is introduced in metered fashion into the second continuous flow reactor at a plurality of spatially separated points along the flow.

5. A process according to claim 1, wherein the epichlorohydrin is introduced through a plurality of spaced apart inlets into the reactor in such a manner that the ratio of glycerin to epichlorohydrin in the vicinity of each inlet is larger than said overall ratio of glycerin to epichlorohydrin.

6. A process according to claim 1, evaporation is carried out so that wherein the epichlorohydrin and ether mixture obtained in the excess glycerin removing step has a glycerin content of less than 20% by weight.

7. A process according to claim 6, evaporation is carried out so that wherein the epichlorohydrin and ether mixture obtained in the excess glycerin removing step has a glycerin content of less than 10% by weight.

8. A process according to claim 1, wherein the evaporating device used in the excess glycerin removing step comprises at least one continuously operating evaporator selected from the group consisting of thin-film evaporators and flash evaporators, and glycerin recovered from the evaporator is recycled to the continuous flow reactor used in the reacting step.

9. A process according to claim 8, wherein the evaporating device comprises a combination of a thin-film evaporator and a flash evaporator.

10. A process according to claim 1, wherein said alkali carbonate solution is an aqueous soda solution having a concentration of more than 1.5 molar.

11. A process according to claim 10, wherein said soda solution has a concentration of more than 2 molar.

12. A process according to claim 1, wherein the alkali hydroxide in the second hydrolysis stage is an aqueous soda lye solution having a concentration of more than 10% by weight.

13. A process according to claim 12, wherein the aqueous soda lye solution has a concentration of more than 35% by weight.

14. A process according to claim 1, wherein the chlorohydrin and ether mixture has a residence time in the first hydrolysis stage of at least one hour and a residence time in the second hydrolysis stage of at least one-half hour.

15. A process according to claim 14, wherein the chlorohydrin and ether mixture has a residence time in the first hydrolysis state of at least one and one-half hours and a residence time in the second hydrolysis stage of at least three-fourths hour.

16. A process according to claim 1, wherein after the addition of mineral acid to the hydrolyzed crude product solution, the resulting solution is concentrated in a flash evaporator and subsequently freed of precipitated salts by filtration or centrifugation.

17. An apparatus for continuously producing diglycerin having a low content of cyclic constituents, said apparatus comprising connected in succession:

at least one continuous flow reactor divided by at least one cross-sectional constriction into at least two reaction zones at different levels therein, said reactor having a lower end with at least one inlet for a stream of glycerin and an acid catalyst and an upper end with at least one outlet for a glycerin/epichlorohydrin reaction mixture, a stirring shaft arranged coaxially and centrally in said reactor with at least one stirring device fastened to said shaft in each reaction zone of the reactor, and an epichlorohydrin supply conduit arranged in said reactor parallel to the stirring shaft and spaced radially outwardly from said at least one stirring device, said supply conduit having at least one outlet opening into each reaction zone of the reactor through which epichlorohydrin can be introduced into the respective reaction zone;

at least one evaporation device for removing excess glycerin, at least one first stage hydrolysis reaction vessel connected to a source of an alkali carbonate solution, at least one second stage hydrolysis reaction vessel connected to a source of an alkali hydroxide, and at least one flash evaporator for removing cyclic diglycerin and unreacted residual glycerin.

18. An apparatus according to claim 17, wherein said evaporating device for removing excess glycerin comprises a continuously operating evaporator selected from thin-film evaporators and flash evaporators.

19. An apparatus according to claim 17, wherein said continuous flow reactor is a vertically arranged flow reactor having a substantially cylindrical reactor housing divided by cross-sectional constrictions into at least 4 reaction zones.

20. An apparatus according to claim 19, wherein the cross-sectional constrictions consist of intermediate base plates, deflecting plates or separator plates provided with a plurality of perforations or through-openings for the reaction mixture.

21. An apparatus according to claim 20, wherein the intermediate base plates, deflecting plates or separator plates have a circular form and are arranged horizontally at different levels in the flow reactor; said plates each having a central opening through which the stirring shaft extends and a second opening through which the epichlorohydrin supply conduit passes.

22. An apparatus according to claim 20, wherein said intermediate base plates, deflecting plates or separator plates each have an outer circumferential edge which is spaced from an adjacent wall of the flow reactor so that an unsealed gap is formed therebetween.

23. An apparatus according to claim 20, wherein the intermediate base plates, deflecting plates or separator plates are spaced approximately the same distance from one another.

24. An apparatus according to claim 17, wherein said outlet openings are constructed as venturi nozzles.

* * * * *